US009309208B2

(12) United States Patent
Biehl et al.

(10) Patent No.: US 9,309,208 B2
(45) Date of Patent: Apr. 12, 2016

(54) METHODS OF MAKING AND USING THIOXOTHIAZOLIDINE AND RHODANINE DERIVATIVES AS HIV-1 AND JSP-1 INHIBITORS

(71) Applicants: Southern Methodist University, Dallas, TX (US); The Johns Hopkins University, Baltimore, MD (US)

(72) Inventors: Edward R. Biehl, Dallas, TX (US); Sukanta Kamila, Dallas, TX (US); Ted M. Dawson, Baltimore, MD (US)

(73) Assignees: Southern Methodist University, Dallas, TX (US); Johns Hopkins University, Baltimore, MD (US)

( * ) Notice: Subject to any disclaimer, the term of this patent is extended or adjusted under 35 U.S.C. 154(b) by 102 days.

(21) Appl. No.: 13/849,339

(22) Filed: Mar. 22, 2013

(65) Prior Publication Data

US 2013/0253021 A1    Sep. 26, 2013

Related U.S. Application Data

(60) Provisional application No. 61/614,563, filed on Mar. 23, 2012.

(51) Int. Cl.
| C07D 417/00 | (2006.01) |
| C07D 277/00 | (2006.01) |
| C07D 277/34 | (2006.01) |
| C07D 277/62 | (2006.01) |
| C07D 417/06 | (2006.01) |
| C07D 417/14 | (2006.01) |

(52) U.S. Cl.
CPC ............ C07D 277/34 (2013.01); C07D 277/62 (2013.01); C07D 417/06 (2013.01); C07D 417/14 (2013.01)

(58) Field of Classification Search
CPC .. C07D 277/36; C07D 277/34; C07D 277/66; C07D 417/02; C07D 417/00; C07D 417/14; C07D 417/06; A61K 31/427; A61K 31/428; A61K 31/4273
USPC .......... 514/369, 367; 548/165, 152, 159, 181, 548/183
See application file for complete search history.

(56) References Cited

U.S. PATENT DOCUMENTS

| 3,759,912 | A | 9/1973 | Derungs |
| 5,116,855 | A | 5/1992 | Inoue et al. |
| 5,696,117 | A | 12/1997 | Frechette et al. |
| 5,707,990 | A | 1/1998 | Frechette et al. |
| 6,713,629 | B2 | 3/2004 | Iwataki et al. |
| 6,849,641 | B1 | 2/2005 | Tang et al. |
| 7,393,869 | B2 | 7/2008 | Zhang et al. |
| 7,872,027 | B2 | 1/2011 | Metallo et al. |
| 2009/0286797 | A1 | 11/2009 | Peters et al. |
| 2012/0245347 | A1 | 9/2012 | Biehl et al. |
| 2012/0245352 | A1 | 9/2012 | Biehl et al. |
| 2014/0135494 | A1 | 5/2014 | Biehl et al. |

FOREIGN PATENT DOCUMENTS

| CN | 1365972 A | 8/2002 |
| KR | 1020110137939 A | 12/2011 |
| WO | 9616964 A1 | 6/1996 |
| WO | 9921859 A1 | 5/1999 |
| WO | 2010044924 A1 | 4/2010 |
| WO | 2013142831 A1 | 9/2013 |

OTHER PUBLICATIONS

Mamedov, Vakhid, A., et al, "Efficient synthesis of 2-(pyrazol-e-yl)benzimidazoles from 3-arylacylidene-3,4- dihydroquinoxalin-2(1H)-ones and hydrazine and hydrate via a novel arrangement," Tetrahedron Letters 50, 2009, 5186-5189.

Xia, Min, et al, "Sulfamic Acid as an Effective Catalyst in Solvent-Free Synthesis of β-Enaminoketone Derivatives and X-ray Crystallography of Their Representatives," Synthetic Communications, 2008, 38:1268-1278.

Andreichikov, et al. [(Aroylpyruvoyl)amino]benzonitriles and 3-phenacylidene-6(7)-cyano-3,4-dihydro-2-quinoxalinones, 1989, Khimiko-Farmatsevticheskii Zhurnal, 23 (8), 946-949.

International Search Report and Written Opinino for PCT/US2013/033584 dated Jul. 18, 2013.

Kamila, S., et al., "An efficient microwave assisted synthesis of novel class of Rhodanine derivatives as potential HIV-1 and JSP-1 Inhibitors," Tetrahedron Letters, 2011, vol. 52, pp. 4375-4377.

Ramkumar, K., et al, "Design, synthesis and structure-activity studies of rhodanine derivatives as HIV-1 integrase inhibitors," Molecules, 2010, vol. 15, pp. 39-58-3992.

Rinaldi, M., et al. "A versatile and practical synthesis toward the development of novel HIV-1 integrase inhibitors,", Chem. Med. Chem., 2011, vol. 6, pp. 343-352.

Balderamos, M., et al., "Synthesis and Structure-Activity Relationship Studies of 3-Substituted Indolin-2-ones as Effective Neuroprotective Agents," the Society for Experimental Biology and Medicine, Jul. 9, 2008, pp. 1395-1402.

*Primary Examiner* — Shengjun Wang
(74) *Attorney, Agent, or Firm* — Chainey P. Singleton; Daniel J. Chalker; Chalker Flores, LLP

(57) ABSTRACT

The present invention provides methods of making and using 5-(2-(indol-3-yl)-2-oxoethylidene)-3-phenyl-2-thioxothiazolidin-4-one derivatives having HIV-1 or JSP-1 inhibitory activity.

2 Claims, 3 Drawing Sheets

METHODS OF MAKING AND USING THIOXOTHIAZOLIDINE AND RHODANINE DERIVATIVES AS HIV-1 AND JSP-1 INHIBITORS

CROSS-REFERENCE TO RELATED APPLICATIONS

This application claims priority based on U.S. Provisional Application No. 61/614,563, filed Mar. 23, 2012. The contents of which is incorporated by reference in its entirety.

STATEMENT OF FEDERALLY FUNDED RESEARCH

This invention was made with government support NIH, Grant No. 1RC2NS064950. The government has certain rights in this invention.

TECHNICAL FIELD OF THE INVENTION

The present invention relates in general to the field of thioxothiazolidine and Rhodanine derivatives, specifically to compositions of matter and methods of making and using thioxothiazolidine and Rhodanine derivatives as potential HIV-1 and JNK-stimulating phosphatase-1 (JSP-1) inhibitors.

INCORPORATION-BY-REFERENCE OF MATERIALS FILED ON COMPACT DISC

None.

BACKGROUND OF THE INVENTION

Without limiting the scope of the invention, its background is described in connection with thiazolidine derivatives. United Nations Program on HIV AIDS (UNAIDS) estimates that approximately 35.2 million people worldwide are living with HIV and more than 25 million people have died of AIDS. Most of the anti-HIV drugs licensed by the United States Food and Drug Administration (FDA) belong to two categories: reverse transcriptase inhibitors (RTI) and protease inhibitors (PI). Combined application of these antiretroviral drugs has shown significant synergistic effects. However, an increasing number of patients with HIV infection/AIDS can no longer use such drugs as a result of drug resistance and serious adverse effects.

U.S. Pat. No. 7,872,027 entitled, "Low molecular weight Myc-max inhibitors" discloses compounds and compositions for interfering with the association of Myc and Max are described herein. These compounds and compositions are useful in methods inhibiting growth or proliferation of a cell. Methods of inhibiting growth or proliferation of a cell are provided, comprising contacting the cell with an amount of a compound that interferes with Myc and Max association effective to inhibit growth or proliferation of the cell.

U.S. Pat. No. 7,393,869 entitled, "Methods of using thiazolidine derivatives to treat cancer or inflammation" discloses using thiazolidine derivatives to treat cancer, inflammation, or other disorders related to the activities of protein phosphatases PTPN12 or PTPN2 in a mammal.

U.S. Pat. No. 5,116,855, entitled, "Rhodanine derivatives and pharmaceutical compositions" discloses a rhodanine derivative of formula (I)

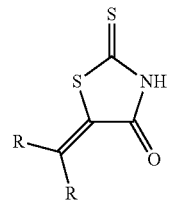

with inhibitory activity against aldose reductase and useful for the prevention or treatment of complications of diabetes.

Although, Rhodanine-based molecules have been used as small molecule inhibitors of numerous targets. Rhodanine and its derivatives possessing hydrogen attached to the nitrogen atom have been patented as fungicides while the compounds containing nitrogen atom were patented as pesticides, with mention being made of their usefulness as fungicides.

For example, U.S. Pat. No. 6,713,629 discloses 5,5-Disubstituted thiazolidine derivative pesticides discloses a fungicidal 5,5-disubstituted thiazolidine derivatives are provided having the formula:

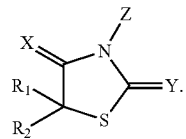

SUMMARY OF THE INVENTION

The present invention provides (Z)-5-(2-(1H-Indol-3-yl)-2-oxoethylidene)-3-phenyl-2-thioxothiazolidin-4-one (compound 7a-q) derivatives synthesized by the condensation reaction of 3-phenyl-2-thioxothiazolidin-4-ones (3a-h) with suitably substituted 2-(1H-indol-3-yl)-2-oxoacetaldehyde (6a-d) under microwave condition. The thioxothiazolidine-4-ones were prepared from the corresponding aromatic amines (compound 1a-e) and di-(carboxymethy)-trithiocarbonyl (2). The aldehydes (compound 6a-h) were synthesized from the corresponding acid chlorides (compound 5a-d) using $HSnBu_3$.

The present invention provides a method of inhibiting one or more enzymes by contacting the one or more enzymes with a compound having a 5-(2-(indol-3-yl)-2-oxoethylidene)-3-phenyl-2-thioxothiazolidin-4-one skeleton wherein the compound has HIV-1 or JSP-1 inhibitory activity.

The one or more enzymes may be HIV-1, JNK-stimulating phosphatase-1 (JSP-1) enzyme or both. And more specifically, the one or more enzymes inhibits an HIV-1 enzyme. The compound is a 5-(2-(indol-3-yl)-2-oxoethylidene)-3-phenyl-2-thioxothiazolidin-4-one comprising a 5-substituted 2-(indol-3-yl) and a 3, 4, 5 substituted phenyl. The compound is (Z)-5-(2-(1H-indol-3-yl)-2-oxoethylidene)-3-phenyl-2-thioxothiazolidin-4-one; (Z)-5-(2-(1H-indol-3-yl)-2-oxoethylidene)-2-thioxo-3-p-tolylthiazolidin-4-one; (Z)-5-(2-(1H-indol-3-yl)-2-oxoethylidene)-3-(3,4-dimethylphenyl)-2-thioxothiazolidin-4-one; (Z)-5-(2-(5-methoxy-1H-indol-3-yl)-2-oxoethylidene)-2-thioxo-3-p-tolylthiazolidin-4-one; (Z)-5-(2-(1H-indol-3-yl)-2-oxoethylidene)-3-(4-methoxyphenyl)-2-thioxothiazolidin-4-one; (Z)-5-(2-(5-methoxy-1H-indol-3-yl)-2-oxoethylidene)-3-(4-methoxyphenyl)-2-thioxothiazolidin-4-one; (Z)-5-(2-(5-methoxy-1H-indol-3-yl)-2-oxoethylidene)-3-phenyl-2-thioxothiazolidin-4-one; (Z)-4-(5-(2-(5-methoxy-1H-indol-3-yl)-2-oxoethylidene)-4-oxo-2-thioxothiazolidin-3-yl)benzonitrile; (Z)-4-(5-(2-(1H- indol-3-yl)-2-oxoethylidene)-4-oxo-2-thioxothiazolidin-3-yl)benzonitrile; (Z)-5-(2-(5-chloro-1H-indol-3-yl)-2-oxoethylidene)-3-phenyl-2-thioxothiazolidin-4-one; (Z)-5-(2-(1H-indol-3-yl)-2-oxoethylidene)-3-(benzo[d]thiazol-6-yl)-2-thioxothiazolidin-4-one; (Z)-5-(2-(1H-indol-3-yl)-2-oxoethylidene)-3-(benzo[d]thiazol-6-yl)-2-thioxothiazolidin-4-one; (Z)-3-(2-(3-(benzo[d]thiazol-6-yl)-4-oxo-2-thioxothiazolidin-5-ylidene)acetyl)-1H-indole-5-carbonitrile; (Z)-5-(2-(1H-indol-3-yl)-2-oxoethylidene)-3-(3,5-dibromo-4-hydroxyphenyl)-2-thioxothiazolidin-4-one; (Z)-5-(2-(1H-indol-3-yl)-2-oxoethylidene)-3-(3,5-dichloro-4-hydroxyphenyl)-2-thioxothiazolidin-4-one; (Z)-3-(3,5-dibromo-4-hydroxyphenyl)-5-(2-(5-methoxy-1H-indol-3-yl)-2-oxoethylidene)-2-thioxothiazolidin-4-one; or (Z)-3-(3,5-dichloro-4-hydroxyphenyl)-5-(2-(5-methoxy-1H-indol-3-yl)-2-oxoethylidene)-2-thioxothiazolidin-4-one.

The present invention also provides a method of modulating the activity of a HIV-1 or a JSP-1 enzyme by contacting the HIV-1 or JSP-1 enzyme with a compound having a 5-(2-(indol-3-yl)-2-oxoethylidene)-3-phenyl-2-thioxothiazolidin-4-one skeleton wherein the compound has HIV-1 or JSP-1 inhibitory activity.

The present invention provides a method of inhibiting HIV-1 or JNK-stimulating phosphatase-1 enzyme by contacting the HIV-1 or JNK-stimulating phosphatase-1 enzyme with a compound of formula (I):

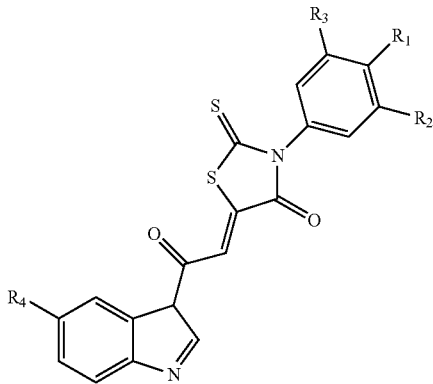

wherein R1, R2, R3 and R4 are independently selected from the group consisting of hydrogen, halo, alkyl, aryl, hydroxyl, alkoxyl, aryloxyl, aralkoxyl, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamido, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylamino-carbonyl, alkylcarbonyloxy, arylcarbonyloxy, carboxyl, alkoxycarbonyl, aryloxycarbonyl, sulfo, alkylsulfonylamido, arylsulfonylamido, alkylsulfonyl, arylsulfonyl, alkylsulfinyl, arylsulfinyl and heteroaryl.

In one embodiment, the R1, R2, R3 and R4 are independently selected from the group comprising H, $CH_3$, $OCH_3$, CN, thiazolidine, OH, Cl, or Br. In another embodiment, the R1 is a H, R2 is a H, R3 is a H, R4 is a H; R1 is a $CH_3$, R2 is a H, R3 is a H, R4 is a H; R1 is a $CH_3$, R2 is a $CH_3$, R3 is a H, R4 is a H; R1 is a $CH_3$, R2 is a H, R3 is a H, R4 is a $OCH_3$; R1 is a $OCH_3$, R2 is a H, R3 is a H, R4 is a H; R1 is a $OCH_3$, R2 is a H, R3 is a H, R4 is a $OCH_3$; R1 is a H, R2 is a H, R3 is a H, R4 is a $OCH_3$; R1 is a CN, R2 is a H, R3 is a H, R4 is a $OCH_3$; R1 is a CN, R2 is a H, R3 is a H, R4 is a H; R1 is a H, R2 is a H, R3 is a H, R4 is a Cl; R1 is a thiazolidine, R2 is a thiazolidine, R3 is a H, R4 is a H; R1 is a thiazolidine, R2 is a thiazolidine, R3 is a H, R4 is a $OCH_3$; R1 is a thiazolidine, R2 is a thiazolidine, R3 is a H, R4 is a CN; R1 is a OH, R2 is a Br, R3 is a Br, R4 is a H; R1 is a OH, R2 is a Cl, R3 is a Cl, R4 is a H; R1 is a OH, R2 is a Br, R3 is a Br, R4 is a $OCH_3$; or R1 is a OH, R2 is a Cl, R3 is a Cl, R4 is a $OCH_3$.

The present invention provides a thioxothiazolidin composition for inhibiting an enzyme comprising: a 5-(2-(indol-3-yl)-2-oxoethylidene)-3-phenyl-2-thioxothiazolidin-4-one skeleton having enzyme inhibitory activity. In one embodiment, the enzyme is HIV-1, JNK-stimulating phosphatase-1 (JSP-1) enzyme or both. In one embodiment, the 5-(2-(indol-3-yl)-2-oxoethylidene)-3-phenyl-2-thioxothiazolidin-4-one skeleton comprising a 5-substituted 2-(indol-3-yl) and a 3, 4, 5 substituted phenyl.

In another embodiment, the 5-(2-(indol-3-yl)-2-oxoethylidene)-3-phenyl-2-thioxothiazolidin-4-one skeleton is selected from (Z)-5-(2-(1H-indol-3-yl)-2-oxoethylidene)-3-phenyl-2-thioxothiazolidin-4-one; (Z)-5-(2-(1H-indol-3-yl)-2-oxoethylidene)-2-thioxo-3-p-tolylthiazolidin-4-one; (Z)-5-(2-(1H-indol-3-yl)-2-oxoethylidene)-3-(3,4-dimethylphenyl)-2-thioxothiazolidin-4-one; (Z)-5-(2-(5-methoxy-1H-indol-3-yl)-2-oxoethylidene)-2-thioxo-3-p-tolylthiazolidin-4-one; (Z)-5-(2-(1H-indol-3-yl)-2-oxoethylidene)-3-(4-methoxyphenyl)-2-thioxothiazolidin-4-one; (Z)-5-(2-(5-methoxy-1H-indol-3-yl)-2-oxoethylidene)-3-(4-methoxyphenyl)-2-thioxothiazolidin-4-one; (Z)-5-(2-(5-methoxy-1H-indol-3-yl)-2-oxoethylidene)-3-phenyl-2-thioxothiazolidin-4-one; (Z)-4-(5-(2-(5-methoxy-1H-indol-3-yl)-2-oxoethylidene)-4-oxo-2-thioxothiazolidin-3-yl)benzonitrile; (Z)-4-(5-(2-(1H-indol-3-yl)-2-oxoethylidene)-4-oxo-2-thioxothiazolidin-3-yl)benzonitrile; (Z)-5-(2-(5-chloro-1H-indol-3-yl)-2-oxoethylidene)-3-phenyl-2-thioxothiazolidin-4-one; (Z)-5-(2-(1H-indol-3-yl)-2-oxoethylidene)-3-(benzo[d]thiazol-6-yl)-2-thioxothiazolidin-4-one; (Z)-5-(2-(1H-indol-3-yl)-2-oxoethylidene)-3-(benzo[d]thiazol-6-yl)-2-thioxothiazolidin-4-one; (Z)-3-(2-(3-(benzo[d]thiazol-6-yl)-4-oxo-2-thioxothiazolidin-5-ylidene)acetyl)-1H-indole-5-carbonitrile; (Z)-5-(2-(1H-indol-3-yl)-2-oxoethylidene)-3-(3,5-dibromo-4-hydroxyphenyl)-2-thioxothiazolidin-4-one; (Z)-5-(2-(1H-indol-3-yl)-2-oxoethylidene)-3-(3,5-dichloro-4-hydroxyphenyl)-2-thioxothiazolidin-4-one; (Z)-3-(3,5-dibromo-4-hydroxyphenyl)-5-(2-(5-methoxy-1H-indol-3-yl)-2-oxoethylidene)-2-thioxothiazolidin-4-one; or (Z)-3-(3,5-dichloro-4-hydroxyphenyl)-5-(2-(5-methoxy-1H-indol-3-yl)-2-oxoethylidene)-2-thioxothiazolidin-4-one.

In one embodiment, the thioxothiazolidin composition of formula (I) for inhibiting an enzyme:

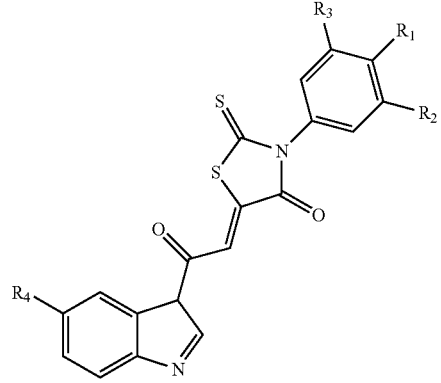

wherein R1, R2, R3 and R4 are independently selected from the group consisting of hydrogen, halo, alkyl, aryl, hydroxyl, alkoxyl, aryloxyl, aralkoxyl, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamido, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylamino-carbonyl, alkylcarbonyloxy, arylcarbonyloxy, carboxyl, alkoxycarbonyl, aryloxycarbonyl, sulfo, alkylsulfonylamido, arylsulfonylamido, alkylsulfonyl, arylsulfonyl, alkylsulfinyl, arylsulfinyl and heteroaryl.

In another embodiment, the enzyme is HIV-1, JNK-stimulating phosphatase-1 (JSP-1) enzyme or both. In another embodiment, the R1, R2, R3 and R4 are independently selected from the group comprising H, CH$_3$, OCH$_3$, CN, thiazolidine, OH, Cl, or Br. In another embodiment, the R1 is a H, R2 is a H, R3 is a H, R4 is a H; R1 is a CH$_3$, R2 is a H, R3 is a H, R4 is a H; R1 is a CH$_3$, R2 is a CH$_3$, R3 is a H, R4 is a H; R1 is a CH$_3$, R2 is a H, R3 is a H, R4 is a OCH$_3$; R1 is a OCH$_3$, R2 is a H, R3 is a H, R4 is a H; R1 is a OCH$_3$, R2 is a H, R3 is a H, R4 is a OCH$_3$; R1 is a H, R2 is a H, R3 is a H, R4 is a OCH$_3$; R1 is a CN, R2 is a H, R3 is a H, R4 is a OCH$_3$; R1 is a CN, R2 is a H, R3 is a H, R4 is a H; R1 is a H, R2 is a H, R3 is a H, R4 is a Cl; R1 is a thiazolidine, R2 is a thiazolidine, R3 is a H, R4 is a H; R1 is a thiazolidine, R2 is a thiazolidine, R3 is a H, R4 is a OCH$_3$; R1 is a thiazolidine, R2 is a thiazolidine, R3 is a H, R4 is a CN; R1 is a OH, R2 is a Br, R3 is a Br, R4 is a H; R1 is a OH, R2 is a Cl, R3 is a Cl, R4 is a H; R1 is a OH, R2 is a Br, R3 is a Br, R4 is a OCH$_3$; or R1 is a OH, R2 is a Cl, R3 is a Cl, R4 is a OCH$_3$.

For example the composition may have the structure:

(SK-T-7a)

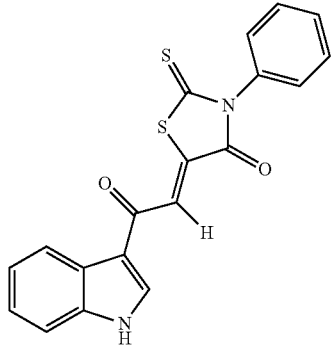

(SK-T-7b)

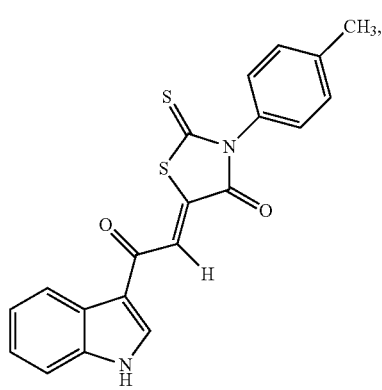

(SK-T-7c)

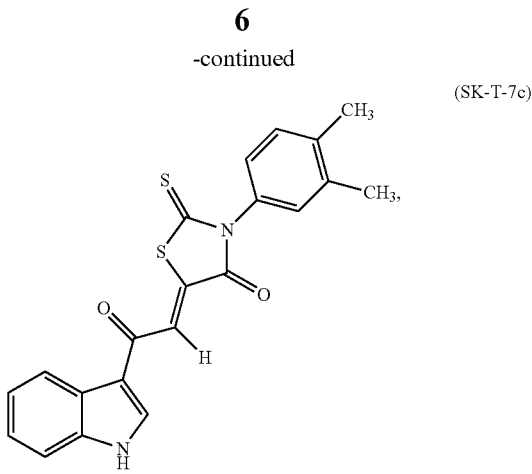

(SK-T-7d)

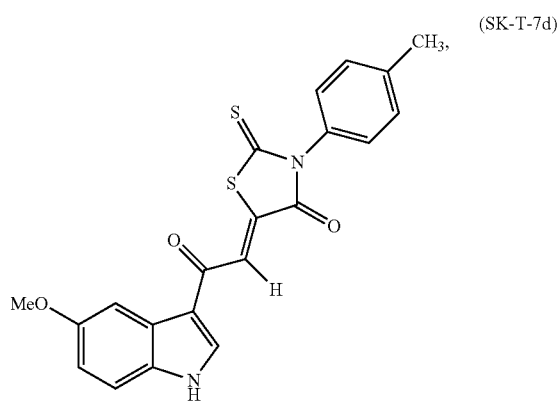

(SK-T-7f)

(SK-T-7e)

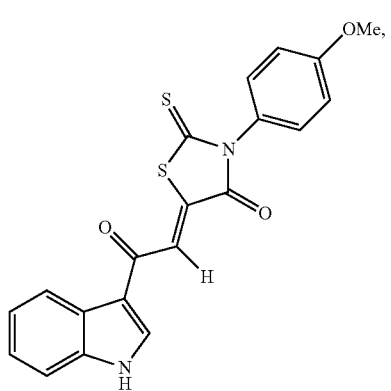

(SK-T-7g)
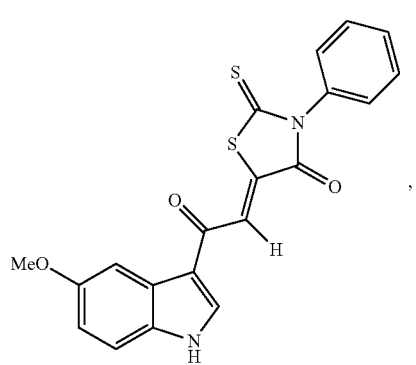
,
(SK-T-7h)
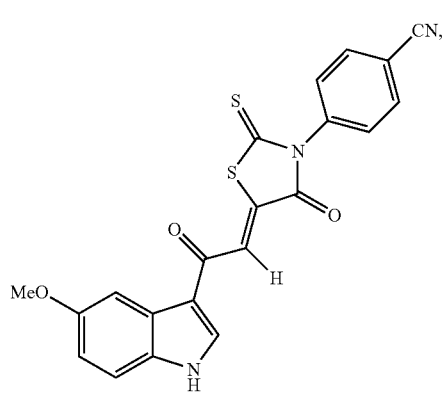
,
(SK-T-7i)
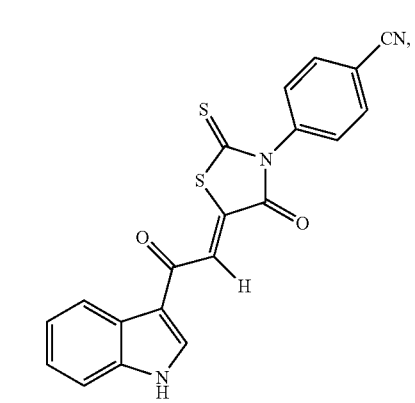
,
(SK-T-7j)
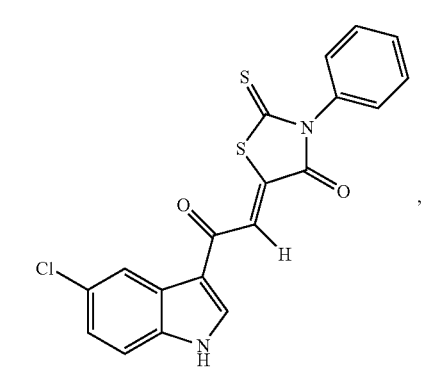
,
(SK-T-7k)
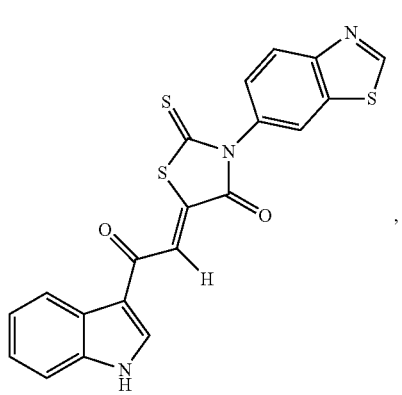
,
(SK-T-7l)
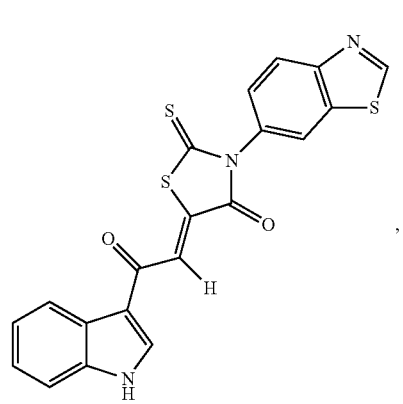
,
(SK-T-7m)
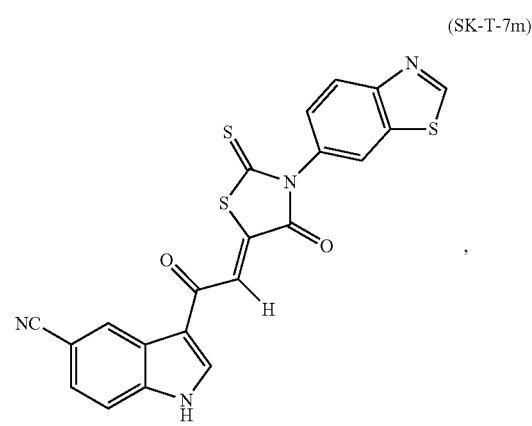
,
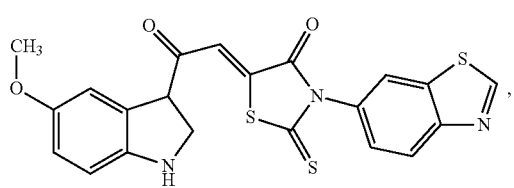

-continued

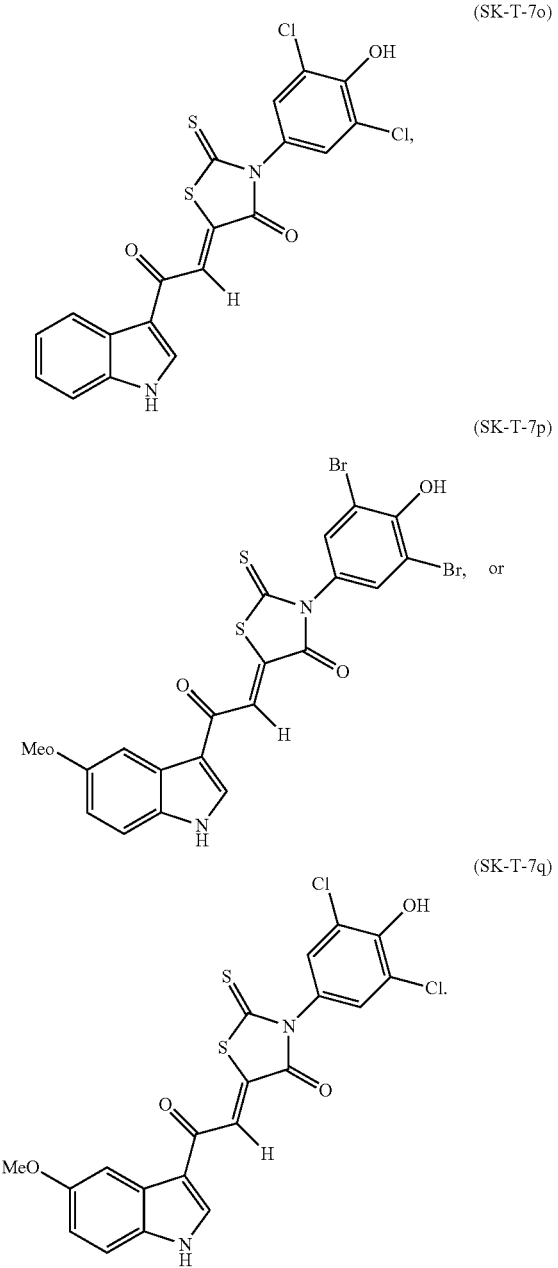

(SK-T-7o)

(SK-T-7p)

(SK-T-7q)

The present invention provides a thioxothiazolidin composition further comprising a pharmaceutical carrier in contact with the thioxothiazolidin composition to make a composition used in the modulating the activity of HIV-1, JNK-stimulating phosphatase-1 (JSP-1) enzyme or both.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
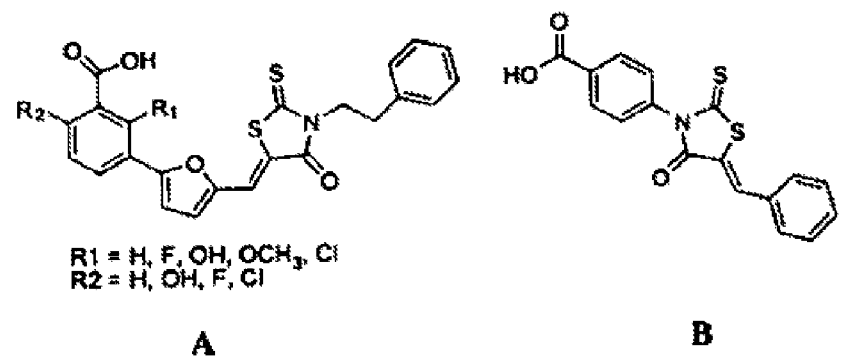
FIGS. 1A and 1B are images of competitive inhibitors of HIV-1 and JSP-1.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

The term "alkylene" refers to a divalent alkyl group as defined above, such as methylene (—CH$_2$—), propylene (—CH2 CH$_2$CH$_2$—), chloroethylene (—CHClCH$_2$—), 2-thiobutene-CH$_2$CH(SH)CH$_2$CH$_2$, 1-bromo-3-hydroxyl-4-methylpentene (—CHBrCH$_2$CH(OH)CH(CH$_3$)CH$_2$—), and the like.

As used herein, the term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

As used herein, the term "amido" denotes an amide linkage: —C(O)NHR (wherein R is hydrogen or alkyl). The term "amino" denotes an amine linkage: —NR—, wherein R is hydrogen or alkyl.

As used herein, the term "aryl" denotes a chain of carbon atoms which form at least one aromatic ring having between about 4-14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "alkoxy" denotes —OR—, wherein R is alkyl.

The term "alkylcarbonyl" denote an alkyl group as defined above substituted with a C(O) group, for example, $CH_3C(O)$—, $CH_3CH_2C(O)$—, etc.

As used herein, the term "alkylcarboxyl" denote an alkyl group as defined above substituted with a C(O)O group, for example, $CH_3C(O)O$—, $CH_3CH_2C(O)O$—, etc.

As used herein, the term "carboxyl" denotes —C(O)O—, and the term "carbonyl" denotes —C(O)—. The term "cycloalkyl" signifies a saturated, cyclic hydrocarbon group with 3-8, preferably 3-6 carbon atoms, i.e. cyclopropyl, cyclobutyl, cyclopentyl and cyclohexyl and the like.

The term "halogen" includes chlorine, fluorine, bromine, iodine and mixtures thereof.

The term "heteroaryl" refers to an aromatic mono- or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are thiophenyl, isoxazolyl, thiazolyl, piperidinyl, pyridinyl, pyrrolyl, imidazolyl, tetrazolyl, preferably pyridinyl, isoxazolyl or thiazolyl. Optionally, the heteroaryl group can be mono-, di- or trisubstituted, independently, with phenyl, alkyl, alkylcarbonyl, alkoxycarbonyl, hydroxy, amino, alkylamino, dialkylamino, carboxy, alkoxycarbonylalkyl, preferably alkyl.

The term "heterocycle" means a straight chain or ring system that may contain from zero to four heteroatoms selected from N, O, and S, wherein the nitrogen and sulfur atoms are optionally oxidized, and the nitrogen atom(s) are optionally quaternized. These groups can be optionally substituted with one or more functional groups as defined under "alkyl" above.

The present invention provides (Z)-5-(2-(1H-Indol-3-yl)-2-oxoethylidene)-3-phenyl-2-thioxothiazolidin-4-one (compound 7a-q) derivatives synthesized by the condensation reaction of 3-phenyl-2-thioxothiazolidin-4-ones (3a-h) with suitably substituted 2-(1H-indol-3-yl)-2-oxoacetaldehyde (6a-d) under microwave condition. The thioxothiazolidine-4-ones were prepared from the corresponding aromatic amines (compound 1a-e) and di-(carboxymethy)-trithiocarbonyl (2). The aldehydes (compound 6a-h) were synthesized from the corresponding acid chlorides (compound 5a-d) using $HSnBu_3$.

As used herein, "pharmaceutically acceptable," means acceptable for use in humans and animals. Excipients include, without limitation, one or more suitable: vehicle(s), solvent(s), diluent(s), pH modifier(s), buffer(s), salt(s), colorant(s), rheology modifier(s), lubricant(s), filler(s), antifoaming agent(s), erodeable polymer(s), hydrogel(s), surfactant(s), emulsifier(s), adjuvant(s), preservative(s), phospholipid(s), fatty acid(s), mono-, di- and tri-glyceride(s) and derivatives thereof, waxe(s), oil(s) and water. The choice of excipient depends on the dosage form in question. Parenteral administration may require at a minimum buffers and salts to match physiological conditions, and thus includes salt and buffer, such as, without limitation, normal saline or phosphate-buffered saline. Depending on the solubility of the compound (active ingredient), the dosage form would be aqueous, micellular (including liposomes) or lipophilic. Formulation of a drug product and choice of suitable excipient(s) with adequate bioavailability is within the average skill of those in the pharmaceutical and formulary arts. The compound may be administered via any useful delivery route, including, without limitation, orally or parenterally, and the drug product/dosage form is tailored to the desired delivery route. For example and without limitation, an HCl salt of a compound described herein may be administered intravenously or intramuscularly in normal saline, or may be administered in tablet or capsule form with appropriate excipients.

As used herein, "modulate" or "modulation" is used to denote the altering of the activity and can be an increase or a decrease the activity when compared to native or normal activity.

The present invention provides a method of inhibiting one or more enzymes by contacting the one or more enzymes with a compound having a 5-(2-(indol-3-yl)-2-oxoethylidene)-3-phenyl-2-thioxothiazolidin-4-one skeleton wherein the compound has HIV-1 or JSP-1 inhibitory activity.

The present invention provides a method of inhibiting HIV-1 or JNK-stimulating phosphatase-1 enzyme by contacting the HIV-1 or JNK-stimulating phosphatase-1 enzyme with a compound of formula (I):

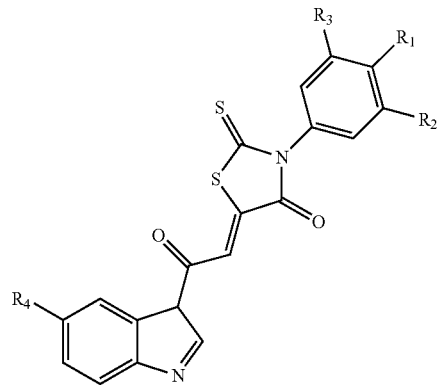

wherein R1, R2, R3 and R4 are independently selected from the group consisting of hydrogen, halo, alkyl, aryl, hydroxyl, alkoxyl, aryloxyl, aralkoxyl, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamido, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylamino-carbonyl, alkylcarbonyloxy, arylcarbonyloxy, carboxyl, alkoxycarbonyl, aryloxycarbonyl, sulfo, alkylsulfonylamido, arylsulfonylamido, alkylsulfonyl, arylsulfonyl, alkylsulfinyl, arylsulfinyl and heteroaryl.

FIGS. 1A and 1B are images of competitive inhibitors of HIV-1 and JSP-1. FIG. 1A illustrates 2-aryl-5-(4-oxo-3-phenethyl-2-thioxothiazolidinylidenemethyl)-furans with Rhodanine as a core molecule exhibiting anti-HIV-1 activity. One embodiment of the competitive inhibitor shown in FIG. 1A includes the core structure shown with the R1 group substituted as a H, F, OH, $OCH_3$, or Cl and the R2 group substituted as a H, OH, F, or Cl. As it is understood, the combinations are derived from the various combinations of R1 substitutions and R2 substitutions. For example, R1 may be a H, and in distinct embodiments R2 may be a H, OH, F, or Cl. Similarly, R1 may be a F and in distinct embodiments R2 may be a H, OH, F, or Cl. R1 may be a OH and in distinct embodiments R2 may be a H, OH, F, or Cl. R1 may be a $OCH_3$ and in distinct embodiments R2 may be a H, OH, F, or Cl. R1 may be a Cl, and in distinct embodiments R2 may be a H, OH, F, or Cl, thus providing numerous different embodiments of the core composition. FIG. 1B is 5-Benzylidine-3-pheny-2-thiox-othiazolidin-4-one core shown to inhibit the Jun $NH_2$-terminal kinase (Jnk) stimulatory phosphatase-1 USP-1.

As stated above, Rhodanine and its derivatives have been used as fungicides and pesticides. However, Rhodanine-based molecules may also be used as small molecule inhibitors of numerous targets such as HCV NS3 protease, aldose reductase p-lactamase, UDP-N-acetylmuramate/L-alanine UDP-N-acetylmuramate/L-alanine ligase, antidiabetic agents, cathepsin D, and histidine decarboxylase. The present invention includes preparing and evaluating the biological importance of these Rhodanine-based molecules and thioxothiazolidine compounds and derivatives thereof. The present invention provides the synthesis of a novel class of Rhodanine-based small molecule with inhibitory properties against JSP-1 and HIV-1 in the low micro molar range.

Figure 2:
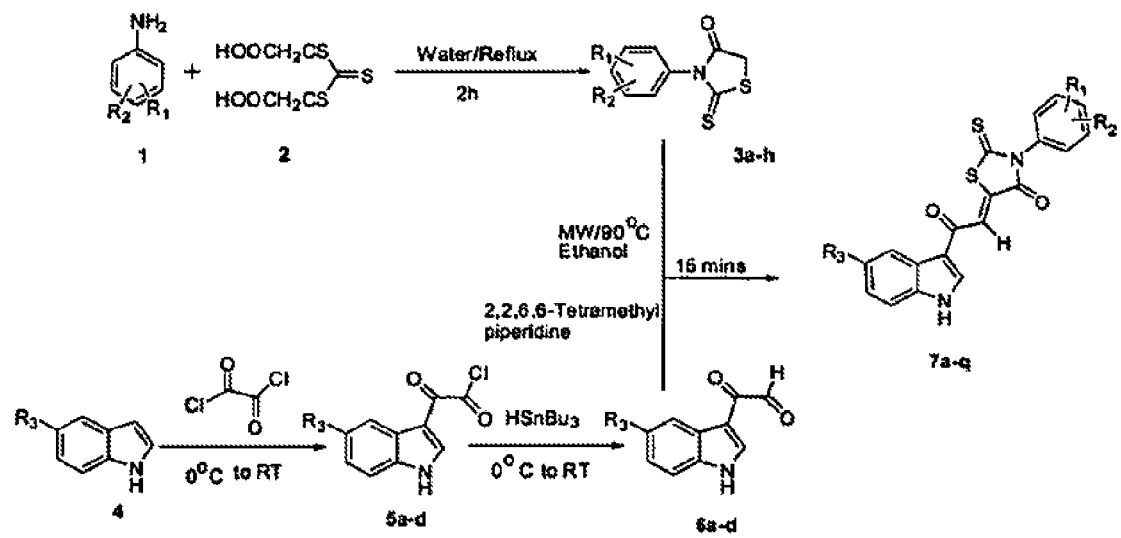
FIG. 2 is an image of a reaction scheme of one of the synthesis for 5-(2-(1H-Indol-3-yl)-2-oxoethylidene)-3-phenyl-2-thiox-othiazolidin-4-ones.

FIG. 2 is the synthesis according to one route for 5-(2-(1H-Indol-3-yl)-2-oxoethylidene)-3-phenyl-2-thiox-othiazolidin-4-ones. 5-(2-(1H-Indol-3-yl)-2-oxoethylidene)-3-phenyl-2-thiox-othiazolidin-4-ones (7a-q) were synthesized by Knoevenagel condensation of 3-phenyl-2-thioxothiazolidin-4-ones (3a-h) derivatives with suit ably substituted 2-(1H-indol-3-yl)-2-oxoacetaldehydes (6a-d) using microwave irradiation and catalytic amounts of 2,2,6,6-tetramethyl piperidine (TMP) in ethanol. Although other bases (Table 1) can be used as catalyst (e.g., piperidine, pyridine. N-methyl piperidine (NMP), DBU), TMP works best.

Figure 3A:
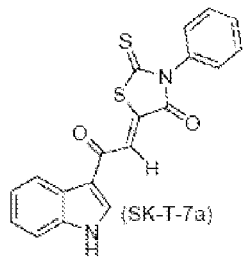
FIGS. 3A to 3Q are images of 2-thioxothiazolidin-4-ones or Rhodanine compounds of the claimed invention.
Figure 3B:
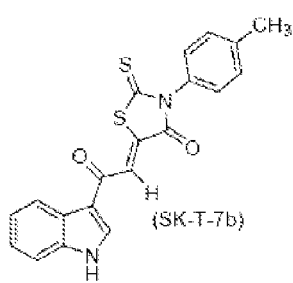
Figure 3C:
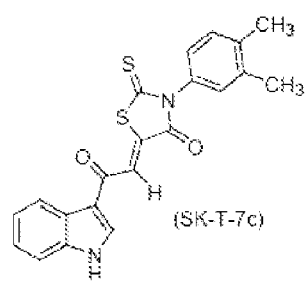
Figure 3D:
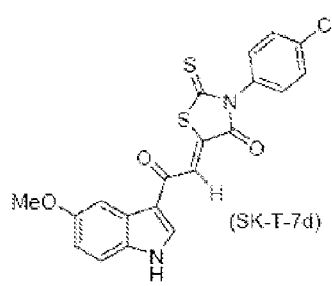
Figure 3E:
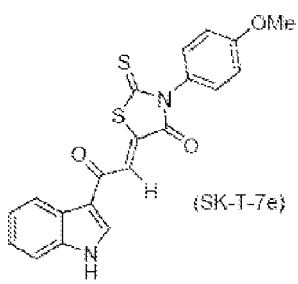
Figure 3F:
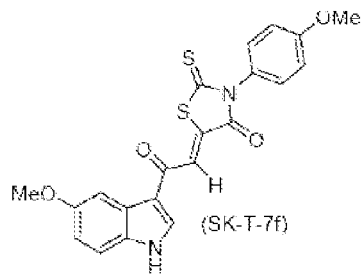
Figure 3G:
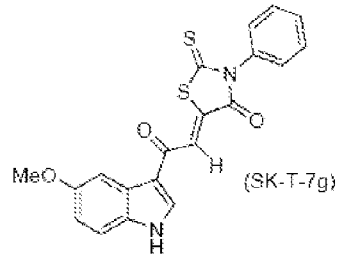
Figure 3H:
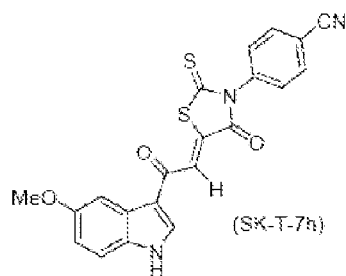
Figure 3I:
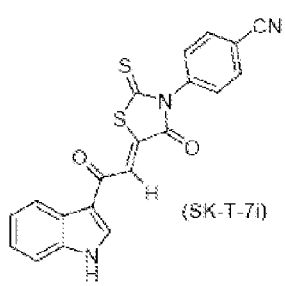
Figure 3J:
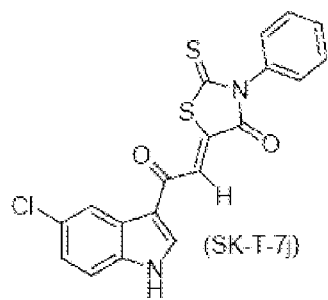
Figure 3K:
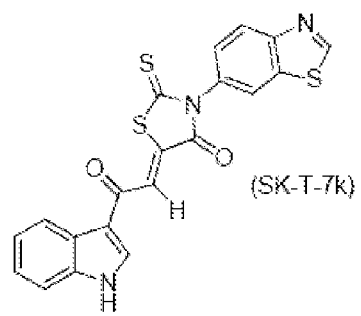
Figure 3L:
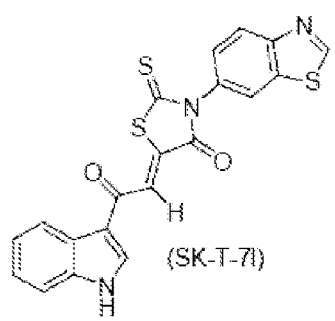
Figure 3M:
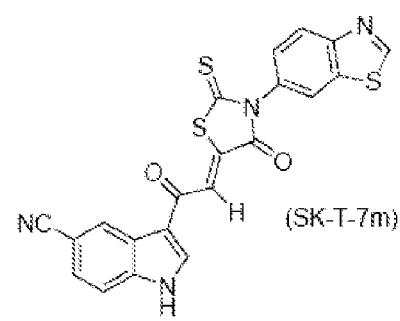
Figure 3N:
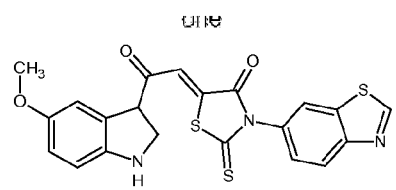
Figure 3O:
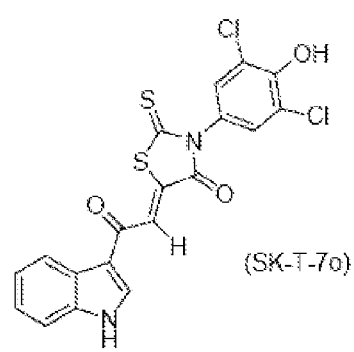
Figure 3P:
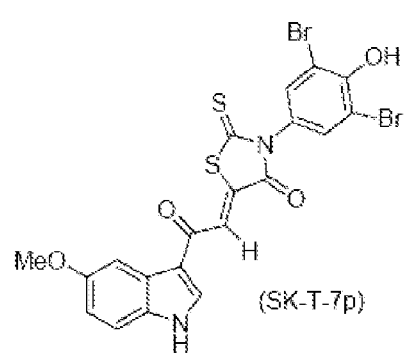
Figure 3Q:
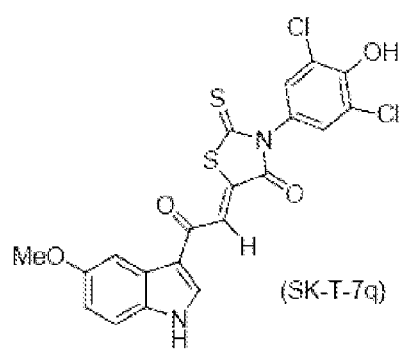

FIGS. 3A to 3Q are images of 2-thioxothiazolidin-4-ones or Rhodanine compounds of the claimed invention.

The optimum temperature and condition for this microwave-assisted reaction were determined by a series of reactions of 3-phenyl-2-thioxothiazolidin-4-one (3b) and 2-(1H-indol-3-yl)-2-oxoacetaldehyde (6a). The results are summarized in Table 1.

TABLE 1

Screening of solvents, reaction time, and temperature for the synthesis of 7b

| Base | Condition[a] | Temp (° C.) | Time (min) | Yield[b] (%) |
|---|---|---|---|---|
| — | No solvent | 90 | 15 | Trace |
| — | Ethanol | 90 | 15 | Trace |
| Piperidene | Ethanol | 90 | 15 | 80 |
| TMP | Ethanol | 90 | 15 | 96 |
| TMP | No solvent | 90 | 15 | Trace |
| DBU/pyridine | Ethanol | 90 | 20 | 20 |
| TMP | Acetonitrile | 90 | 15 | 76 |
| TMP | Acetonitrile | 130 | 15 | 15 |
| DBU | Acetonitrile | 90 | 30 | Trace |
| TMP | DMF | 90 | 15 | 45 |
| NMP | DMF | 90 | 30 | 10 |
| DBU | DMF | 120-40 | 15 | Trace |
| TMP | Water | 90 | 15 | Trace |
| TMP | Water | 130 | 15 | Trace |
| — | Water | 130 | 30 | Trace |
| TMP | Toluene | 90 | 15 | Trace |
| TMP | Isopropanol | 90 | 15 | 45 |
| TMP | THF | 90 | 15 | 38 |
| TMP | n-Butanol | 90 | 15 | 33 |

[a] All the reaction was carried out in equimolar amounts of each compound in 2 ml of solvent at 150 psi pressure.
[b] Isolated yield.

The same reaction under a conventional reflux condition using ethanol as solvent gave lower yields of between about 11 to 69% in a longer time of about 5 hours and/or compounds requiring rigorous purification. However, the microwave reaction of the present invention provides cleaner reaction in a shorter time of 15 minutes time, and the products were only required to be washed with cold ethanol. The yields are good to excellent as seen in Table 1.

As shown in Table 1, it is clear that microwave irradiation at 90° C. for 15 minutes in ethanol is the optimum condition for the synthesis of these molecules.

All the compounds 7a-q were isolated as a single (Z) isomer and were confirmed by comparing the vinylic proton shift in $^1$H NMR with previously reported data which appears around δ 8.00 ppm. The starting materials 3a-h were synthesized, and the structures are listed in Table 2 below:

TABLE 2

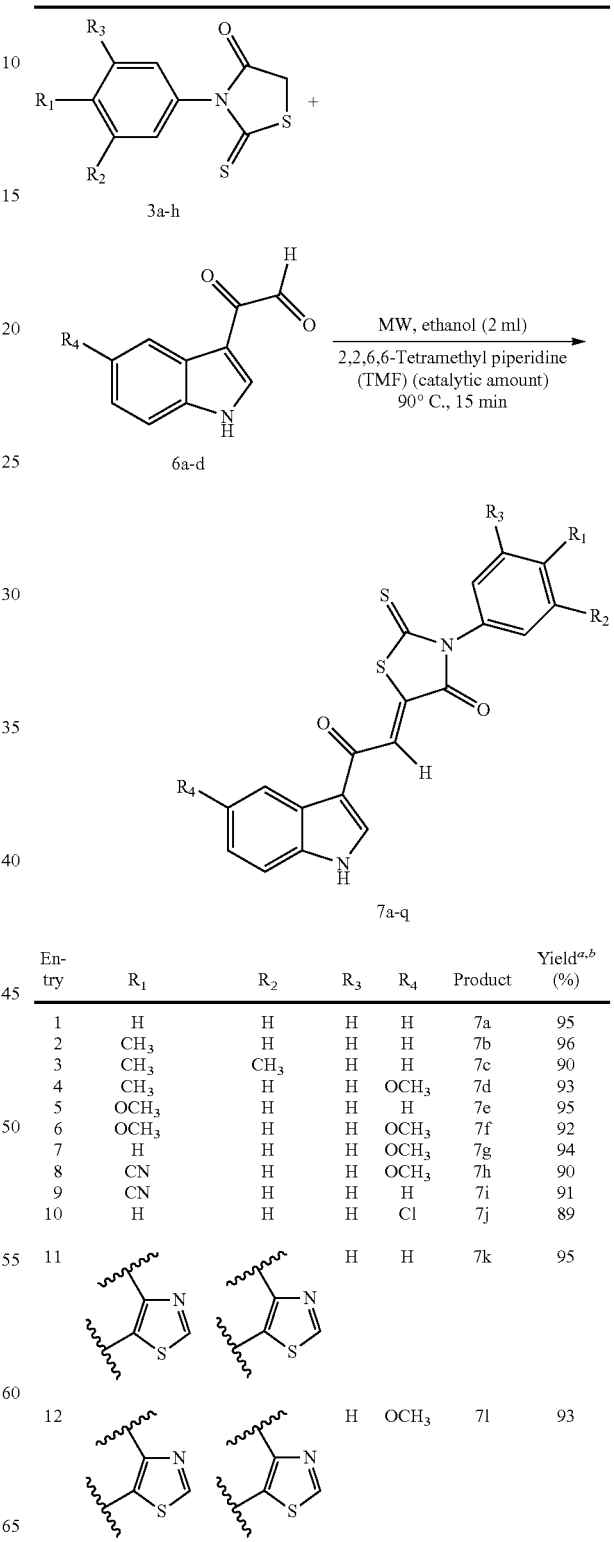

| Entry | $R_1$ | $R_2$ | $R_3$ | $R_4$ | Product | Yield[a,b] (%) |
|---|---|---|---|---|---|---|
| 1 | H | H | H | H | 7a | 95 |
| 2 | CH$_3$ | H | H | H | 7b | 96 |
| 3 | CH$_3$ | CH$_3$ | H | H | 7c | 90 |
| 4 | CH$_3$ | H | H | OCH$_3$ | 7d | 93 |
| 5 | OCH$_3$ | H | H | H | 7e | 95 |
| 6 | OCH$_3$ | H | H | OCH$_3$ | 7f | 92 |
| 7 | H | H | H | OCH$_3$ | 7g | 94 |
| 8 | CN | H | H | OCH$_3$ | 7h | 90 |
| 9 | CN | H | H | H | 7i | 91 |
| 10 | H | H | H | Cl | 7j | 89 |
| 11 | (thiazole) | (thiazole) | H | H | 7k | 95 |
| 12 | (thiazole) | (thiazole) | H | OCH$_3$ | 7l | 93 |

TABLE 2-continued

| 13 | [thiazole structure] | H | CN | 7m | 91 |
| 14 | OH | Br | Br | H | 7n | 90 |
| 15 | OH | Cl | Cl | H | 7o | 89 |
| 16 | OH | Br | Br | OCH$_3$ | 7p | 95 |
| 17 | OH | Cl | Cl | OCH$_3$ | 7q | 90 |

$^a$Isolated yield.
$^b$All the compounds were characterized by $^1$H NMR, $^{13}$C NMR, DEPT-135, IR and HRMS analysis.

Referring now to Table 3, compounds 7a-q were obtained in 89-96% yields with high melting point (>300° C.). They were insoluble in usual organic solvent, water, or hexane. The IR (KBr) spectra of compounds 7a-q exhibit absorption bands due to the stretching vibrations of the NH group of indole cycles (3200 cm$^{-1}$ range).

TABLE 3

[Reaction scheme: aromatic amine 1 + di-(carboxymethyl)-trithiocarbonyl 2 → 3a-h, Water, reflux/2 h]

| Entry | R$_1$ | R$_2$ | R$_3$ | Time (h) | Product | Yield$^a$ (%) |
|---|---|---|---|---|---|---|
| 1 | H | H | H | 3.0 | 3a | 75 |
| 2 | CH$_3$ | H | H | 2.5 | 3b | 73 |
| 3 | CH$_3$ | CH$_3$ | H | 2.5 | 3c | 76 |
| 4 | OCH$_3$ | H | H | 2.0 | 3d | 75 |
| 5 | CN | H | H | 4.0 | 3e | 71 |
| 6 | OH | Br | Br | 3.0 | 3f | 78 |
| 7 | OH | Cl | Cl | 3.0 | 3g | 76 |
| 8 | [thiazole structure] | | H | 4.0 | 3h | 75 |

The spectra of compounds 7a-q display characteristic bands and C=S group (intense bands at 1628-1610 cm$^{-1}$). The 3-phenyl due to stretching vibrations of two C=O groups (1720 cm$^{-1}$ range). -2-thioxothiazolidin-4-ones (3a-b) derivatives were prepared by refluxing equimolar amounts of suitably substituted aromatic amines (1a-e) and di-(carboxymethyl)-trithiocarbonyl (2). The aldehydes 6a-d were synthesized by treating corresponding acid chlorides with HSnBu$_3$. The acid chlorides were prepared by acylation of indole (or substituted indole) with oxalylchloride. All compounds were characterized by $^1$H NMR, $^{13}$C NMR, DEPT-135, IR and HRMS studies.

The present invention provides a novel series of (Z)-5-(2-(1H-indol-3-yl)-2-oxoethylidene)-3-phenyl-2-thioxothiazolidin-4-one (7a-q) derivatives. The mild reaction conditions, easy workup, good to excellent yields, and easily available substrate make this reaction an attractive method for the preparation of 3-phenyl-2-thioxothiazolidin-4-ones.

The present invention provides the synthesis of drug molecules with a Rhodanine moiety by microwave irradiation and includes (Z)-5-(2-(1H-indol-3-yl)-2-oxoethylidene)-3-phenyl-2-thioxothiazolidin-4-one; (Z)-5-(2-(1H-indol-3-yl)-2-oxoethylidene)-2-thioxo-3-p-tolylthiazolidin-4-one; (Z)-5-(2-(1H-indol-3-yl)-2-oxoethylidene)-3-(3,4-dimethylphenyl)-2-thioxothiazolidin-4-one; (Z)-5-(2-(5-methoxy-1H-indol-3-yl)-2-oxoethylidene)-2-thioxo-3-p-tolylthiazolidin-4-one; (Z)-5-(2-(1H-indol-3-yl)-2-oxoethylidene)-3-(4-methoxyphenyl)-2-thioxothiazolidin-4-one; (Z)-5-(2-(5-methoxy-1H-indol-3-yl)-2-oxoethylidene)-3-(4-methoxyphenyl)-2-thioxothiazolidin-4-one; (Z)-5-(2-(5-methoxy-1H-indol-3-yl)-2-oxoethylidene)-3-phenyl-2-thioxothiazolidin-4-one; (Z)-4-(5-(2-(5-methoxy-1H-indol-3-yl)-2-oxoethylidene)-4-oxo-2-thioxothiazolidin-3-yl)benzonitrile; (Z)-4-(5-(2-(1H-indol-3-yl)-2-oxoethylidene)-4-oxo-2-thioxothiazolidin-3-yl)benzonitrile; (Z)-5-(2-(5-chloro-1H-indol-3-yl)-2-oxoethylidene)-3-phenyl-2-thioxothiazolidin-4-one; (Z)-5-(2-(1H-indol-3-yl)-2-oxoethylidene)-3-(benzo[d]thiazol-6-yl)-2-thioxothiazolidin-4-one; (Z)-5-(2-(1H-indol-3-yl)-2-oxoethylidene)-3-(benzo[d]thiazol-6-yl)-2-thioxothiazolidin-4-one; (Z)-3-(2-(3-(benzo[d]thiazol-6-yl)-4-oxo-2-thioxothiazolidin-5-ylidene)acetyl)-1H-indole-5-carbonitrile; (Z)-5-(2-(1H-indol-3-yl)-2-oxoethylidene)-3-(3,5-dibromo-4-hydroxyphenyl)-2-thioxothiazolidin-4-one; (Z)-5-(2-(1H-indol-3-yl)-2-oxoethylidene)-3-(3,5-dichloro-4-hydroxyphenyl)-2-thioxothiazolidin-4-one; (Z)-3-(3,5-dibromo-4-hydroxyphenyl)-5-(2-(5-methoxy-1H-indol-3-yl)-2-oxoethylidene)-2-thioxothiazolidin-4-one; and (Z)-3-(3,5-dichloro-4-hydroxyphenyl)-5-(2-(5-methoxy-1H-indol-3-yl)-2-oxoethylidene)-2-thioxothiazolidin-4-one.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:
1. A thioxothiazolidin compound of formula (I):

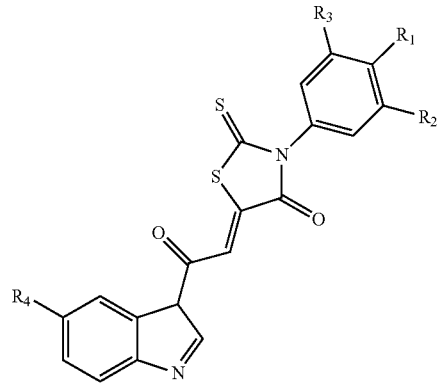

wherein $R_1$, $R_2$, $R_3$ and $R_4$ are independently selected from the group consisting of hydrogen, halo, alkyl, aryl, hydroxyl, alkoxyl, aryloxyl, aralkoxyl, cyano, nitro, alkylcarbamido, arylcarbamido, dialkylcarbamido, diarylcarbamido, alkylarylcarbamido, alkylthiocarbamido, arylthiocarbamido, dialkylthiocarbamido, diarylthiocarbamido, alkylarylthiocarbamidb, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylamino-carbonyl, alkylcarbonyloxy, arylcarbonyloxy, carboxyl, alkoxycarbonyl, aryloxycarbonyl, sulfo, alkylsulfonylamido, arylsulfonylamido, alkylsulfonyl, arylsulfonyl, alkylsulfinyl, arylsulfinyl and heteroaryl.

2. A thioxothiazolidin compound is selected from (Z)-5-(2-(1H-indol-3-yl)-2-oxoethylidene)-3-phenyl-2-thioxothiazolidin-4-one; (Z)-5-(2-(1H-indol-3-yl)-2-oxoethylidene)-2-thioxo-3-p-tolylthiazolidin-4-one; (Z)-5-(2-(1H-indol-3-yl)-2-oxoethylidene)-3-(3,4-dimethylphenyl)-2-thioxothiazolidin-4-one; (Z)-5-(2-(5-methoxy-1H-indol-3-yl)-2-oxoethylidene)-2-thioxo-3-p-tolylthiazolidin-4-one; (Z)-5-(2-(1H-indol-3-yl)-2-oxoethylidene)-3-(4-methoxyphenyl)-2-thioxothiazolidin-4-one; (Z)-5-(2-(5-methoxy-1H-indol-3-yl)-2-oxoethylidene)-3-(4-methoxyphenyl)-2-thioxothiazolidin-4-one; (Z)-5-(2-(5-methoxy-1H-indol-3-yl)-2-oxoethylidene)-3-phenyl-2-thioxothiazolidin-4-one; (Z)-4-(5-(2-(5-methoxy-1H-indol-3-yl)-2-oxoethylidene)-4-oxo-2-thioxothiazolidin-3-yl)benzonitrile; (Z)-4-(5-(2-(1H-indol-3-yl)-2-oxoethylidene)-4-oxo-2-thioxothiazolidin-3-yl)benzonitrile; (Z)-5-(2-(5-chloro-1H-indol-3-yl)-2-oxoethylidene)-3-phenyl-2-thioxothiazolidin-4-one; (Z)-5-(2-(1H-indol-3-yl)-2-oxoethylidene)-3-(benzo[d]thiazol-6-yl)-2-thioxothiazolidin-4-one; (Z)-5-(2-(1H-indol-3-yl)-2-oxoethylidene)-3-(benzo[d]thiazol-6-yl)-2-thioxothiazolidin-4-one; (Z)-3-(2-(3-(benzo[d]thiazol-6-yl)-4-oxo-2-thioxothiazolidin-5-ylidene)acetyl)-1H-indole-5-carbonitrile; (Z)-5-(2-(1H-indol-3-yl)-2-oxoethylidene)-3-(3,5-dibromo-4-hydroxyphenyl)-2-thioxothiazolidin-4-one; (Z)-5-(2-(1H-indol-3-yl)-2-oxoethylidene)-3-(3,5-dichloro-4-hydroxyphenyl)-2-thioxothiazolidin-4-one; (Z)-3-(3,5-dibromo-4-hydroxyphenyl)-5-(2-(5-methoxy-1H-indol-3-yl)-2-oxoethylidene)-2-thioxothiazolidin-4-one; or (Z)-3-(3,5-dichloro-4-hydroxyphenyl)-5-(2-(5-methoxy-1H-indol-3-yl)-2-oxoethylidene)-2-thioxothiazolidin-4-one.

* * * * *